US00PP21336P2

(12) United States Plant Patent
Vlielander

(10) Patent No.: US PP21,336 P2
(45) Date of Patent: Sep. 28, 2010

(54) ***KALANCHOE* PLANT NAMED 'FUJI-SAN'**

(50) Latin Name: *Kalanchoe blossfeldiana*
Varietal Denomination: Fuji-San

(75) Inventor: Ike J. Vlielander, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 12/456,339

(22) Filed: Jun. 15, 2009

(51) Int. Cl.
*A01H 5/00* (2006.01)

(52) U.S. Cl. ..... Plt./338
(58) Field of Classification Search ..... Plt./338
See application file for complete search history.

*Primary Examiner*—Annette H Para
(74) *Attorney, Agent, or Firm*—C. A. Whealy

(57) ABSTRACT

A new and distinct cultivar of *Kalanchoe* plant named 'Fuji-San', characterized by its compact, upright and uniform plant habit; moderately vigorous growth habit; freely branching plant habit; dark green-colored leaves; uniform, freely and early flowering habit; bright yellow-colored flowers; and excellent postproduction longevity.

1 Drawing Sheet

Botanical designation: *Kalanchoe blossfeldiana.*
Cultivar denomination: 'Fuji-San'.

BACKGROUND OF THE INVENTION

The present invention relates to a new and distinct cultivar of *Kalanchoe* plant, botanically known as *Kalanchoe blossfeldiana*, and hereinafter referred to by the name 'Fuji-San'.

The new *Kalanchoe* is a product of a planned breeding program conducted by the Inventor in De Lier, The Netherlands. The objective of the breeding program is to create new freely-branching and freely- flowering *Kalanchoe* cultivars with attractive foliage and flower coloration.

The new *Kalanchoe* plant originated from a cross-pollination made by the Inventor in De Lier, The Netherlands in 2003, of a proprietary *Kalanchoe blossfeldiana* selection identified as code number 5036 (02), not patented, as the female, or seed, parent with a proprietary *Kalanchoe blossfeldiana* selection identified as code number 5052 (02), not patented, as the male, or pollen, parent. The new *Kalanchoe* was discovered and selected by the Inventor as a single flowering plant from within the progeny of the stated cross-pollination in a controlled environment in De Lier, The Netherlands.

Asexual reproduction of the new *Kalanchoe* plant by vegetative terminal cuttings in a controlled environment in De Lier, The Netherlands since 2005, has shown that the unique features of this new *Kalanchoe* plant are stable and reproduced true to type in successive generations.

SUMMARY OF THE INVENTION

Plants of the new *Kalanchoe* have not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Fuji-San'. These characteristics in combination distinguish 'Fuji-San' as a new and distinct cultivar of *Kalanchoe:*

1. Compact, upright and uniform plant habit.
2. Moderately vigorous growth habit.
3. Freely branching plant habit.

4. Dark green-colored leaves.
5. Uniform, freely and early flowering habit.
6. Bright yellow-colored flowers.
7. Excellent postproduction longevity.

Plants of the new *Kalanchoe* can be compared to plants of the female parent selection. Plants of the new *Kalanchoe* differ from plants of the female parent selection in the following characteristics:

1. Plants of the new *Kalanchoe* are more compact than plants of the female parent selection.
2. Flower stems of plants of the new *Kalanchoe* do not stretch whereas flower stems of plants of the female parent selection have a tendency to stretch.
3. Plants of the new *Kalanchoe* have lighter-colored flowers than plants of the female parent selection.

Plants of the new *Kalanchoe* can be compared to plants of the male parent selection. Plants of the new *Kalanchoe* differ from plants of the male parent selection in the following characteristics:

1. Plants of the new *Kalanchoe* are more freely branching than plants of the male parent selection.
2. Plants of the new *Kalanchoe* have smaller flowers than plants of the male parent selection.
3. Plants of the new *Kalanchoe* have lighter-colored flowers than plants of the male parent selection.

Plants of the new *Kalanchoe* can be compared to plants of the *Kalanchoe blossfeldiana* 'Gelai', disclosed in U.S. Plant Pat. No. 13,367. In side-by-side comparisons conducted in De Lier, The Netherlands, plants of the new *Kalanchoe* differed from plants of 'Gelai' in the following characteristics:

1. Plants of the new *Kalanchoe* were more compact than and not as vigorous as plants of 'Gelai'.
2. Plants of the new *Kalanchoe* had shorter leaves than plants of 'Gelai'.
3. Flower stems of plants of the new *Kalanchoe* did not stretch whereas flower stems of plants of 'Gelai' had a tendency to stretch.
4. Plants of the new *Kalanchoe* and 'Gelai' differed in flower color as plants of 'Gelai' had lighter yellow-colored flowers.

BRIEF DESCRIPTION OF THE PHOTOGRAPH

The accompanying colored photograph illustrates the overall appearance of the new *Kalanchoe* plant, showing the colors as true as it is reasonably possible to obtain in colored reproductions of this type. Colors in the photograph may differ slightly from the color values cited in the detailed botanical description which accurately describe the colors of the new *Kalanchoe* plant. The photograph comprises a side perspective view of a typical flowering plant of 'Fuji-San' grown in a container.

DETAILED BOTANICAL DESCRIPTION

The aforementioned photograph and following observations, measurements and values describe plants grown in De Lier, The Netherlands in a glass-covered greenhouse during the spring and under conditions which closely approximate commercial Kalanchoe production. During the production of the plants, day and night temperatures ranged from 19° C. to 26° C., night temperatures ranged from 20° C. to 21° C. and light levels ranged from 10,000 lux to 50,000 lux. Plants were grown in 10-cm containers and received long day/short night conditions (more than 14 hours of light) for about four weeks; plants then received photoinductive short day/long night conditions (minimum 14 hours darkness) until flowering. Plants were 14 weeks old when the photograph and the description were taken. In the detailed description, color references are made to The Royal Horticultural Society Colour Chart, 1995 Edition, except where general terms of ordinary dictionary significance are used.

Botanical classification: *Kalanchoe blossfeldiana* 'Fuji-San'.

Parentage:

*Female, or seed, parent.*—Proprietary *Kalanchoe blossfeldiana* selection identified as code number 5036 (02), not patented.

*Male or pollen parent.*—Proprietary *Kalanchoe blossfeldiana* selection identified as code number 5052 (02), not patented.

Propagation:

*Type.*—By vegetative terminal cuttings.

*Time to initiate roots, summer.*—About 12 days at temperatures of 21° C.

*Time to initiate roots, winter.*—About 15 days at temperatures of 21° C.

*Time to produce a rooted young plant, summer.*—About 23 days at temperatures of 21° C.

*Time to produce a rooted young plant, winter.*—About 30 days at temperatures of 21° C.

*Root description.*—Fine, fibrous; greyish white in color.

*Rooting habit.*—Freely branching; dense.

Plant description:

*Plant habit.*—Compact, upright and uniform plant habit; freely flowering habit with numerous compound cymes; inverted triangle with rounded crown; appropriate for 10-cm to 15-cm containers; moderately vigorous growth habit.

*Plant height at flowering.*—About 16 cm.

*Plant diameter at flowering.*—About 15 cm.

*Branching habit.*—Freely branching, usually about five to six lateral branches develop per plant; pinching (removal of the terminal apex) is not required but will enhance lateral branch development.

Lateral branch description:

*Length.*—About 11 cm to 14 cm.

*Diameter.*—About 3 mm to 6 mm.

*Internode length.*—About 2 cm to 3 cm.

*Aspect.*—Erect.

*Strength.*—Moderately strong.

*Texture.*—Smooth, glabrous.

*Color.*—Close to 146A.

Foliage description:

*Arrangement.*—Opposite, simple; generally symmetrical.

*Quantity per plant.*—About 7 to 11 mature leaves and about 14 to 18 generative leaves.

*Length.*—About 10.5 cm.

*Width.*—About 8 cm.

*Shape.*—Ovate to elliptic.

*Apex.*—Obtuse.

*Base.*—Obtuse.

*Margin.*—Crenate.

*Texture, upper and lower surfaces.*—Smooth, glabrous; coriaceous; succulent.

*Venation pattern.*—Pinnate.

*Color.*—Developing and fully developed leaves, upper surface: Close to 137A; venation, close to 137A to 137B. Developing and fully developed foliage, lower surface: Close to 137B; venation, close to 137B.

*Petiole.*—Length: About 1 cm. Diameter: About 3 mm to 7 mm. Texture, upper and lower surfaces: Smooth, glabrous. Color, upper and lower surfaces: Close to 137A to 137B.

Flower description:

*Flower arrangement and habit.*—Flowers arranged singly in compound dichasial cymes that arise from leaf axils; uniform and freely flowering habit with usually about 25 open flowers and about 25 flower buds per lateral branch and more than 150 open flowers and flower buds per plant; flowering continuously for at least seven weeks.

*Fragrance.*—None detected.

*Natural flowering season.*—Plants of the new *Kalanchoe* initiate and develop flowers under short day/long night conditions or during November and December in The Netherlands; flower initiation and development can also be induced under artificial short day/long conditions (at least 14 hours of darkness).

*Time to flower.*—Early flowering habit; under short day/long night photoinductive conditions, about nine to eleven weeks are required; actual time to flower is primarily dependent upon temperature and light intensity.

*Post-production longevity.*—Excellent post-production longevity; plants maintain good foliage and flower substance for about 41 days under interior environmental conditions; individual flowers last about 16 days on the plant; flowers persistent.

*Flower diameter.*—About 1.6 cm.

*Flower length (height).*—About 1.2 cm.

*Flower bud.*—Shape: Initially oblong, becoming tubular ovoid with development. Length: About 1 cm. Diameter: About 2.5 mm. Color: Close to 10C.

*Petals.*—Arrangement: Four fused at the base. Length: About 7 mm. Width: About 5.5 mm. Aspect: Flat to partially upright. Shape: Ovate. Apex: Acute. Margin: Entire. Texture, upper and lower surfaces: Smooth, glabrous. Color: When opening, upper surface: Close to 13B. When opening, lower surface: Close to 14D. Fully opened, upper surface: Close to 12A; color becoming closer to 11A with development. Fully opened, lower surface: Close to 14D.

*Sepals.*—Appearance: Four fused at the base. Length: About 6 mm. Width: About 2 mm. Shape: Oblong, pointed. Apex: Acute. Base: Obtuse. Margin: Entire. Aspect: Upright. Texture, immature and mature, upper and lower surfaces: Smooth; glabrous. Color, upper and lower surfaces: Close to 137D.

*Peduncles.*—Length: About 3 mm to 6 mm. Diameter: About 1 mm. Aspect: Erect. Strength: Strong. Texture: Smooth, glabrous. Color: Close to 137C.

*Reproductive organs.*—Androecium: Stamen number: About eight per flower. Anther shape: Elliptic, flat. Anther length: About 0.3 mm. Anther color: Close to 150D. Amount of pollen: Scarce. Pollen color: Close to 12A. Gynoecium: Pistil number: About four per flower. Pistil length: About 1 mm. Style length: About 1 mm. Style color: Close to 138D. Stigma shape: Flat. Stigma color: Close to 8D. Ovary color: Close to 138D.

*Seed.*—Length: About 0.1 mm. Diameter: About 0.05 mm. Color: Close to 166C.

Temperature tolerance: Plants of the new *Kalanchoe* have been observed to tolerate temperatures from about 16° C. to about 35° C.

Pathogen/pest resistance: Plants of the new *Kalanchoe* have not been observed to be resistant to pests and pathogens common to *Kalanchoes.*

It is claimed:

1. A new and distinct *Kalanchoe* plant named 'Fuji-San' as illustrated and described.

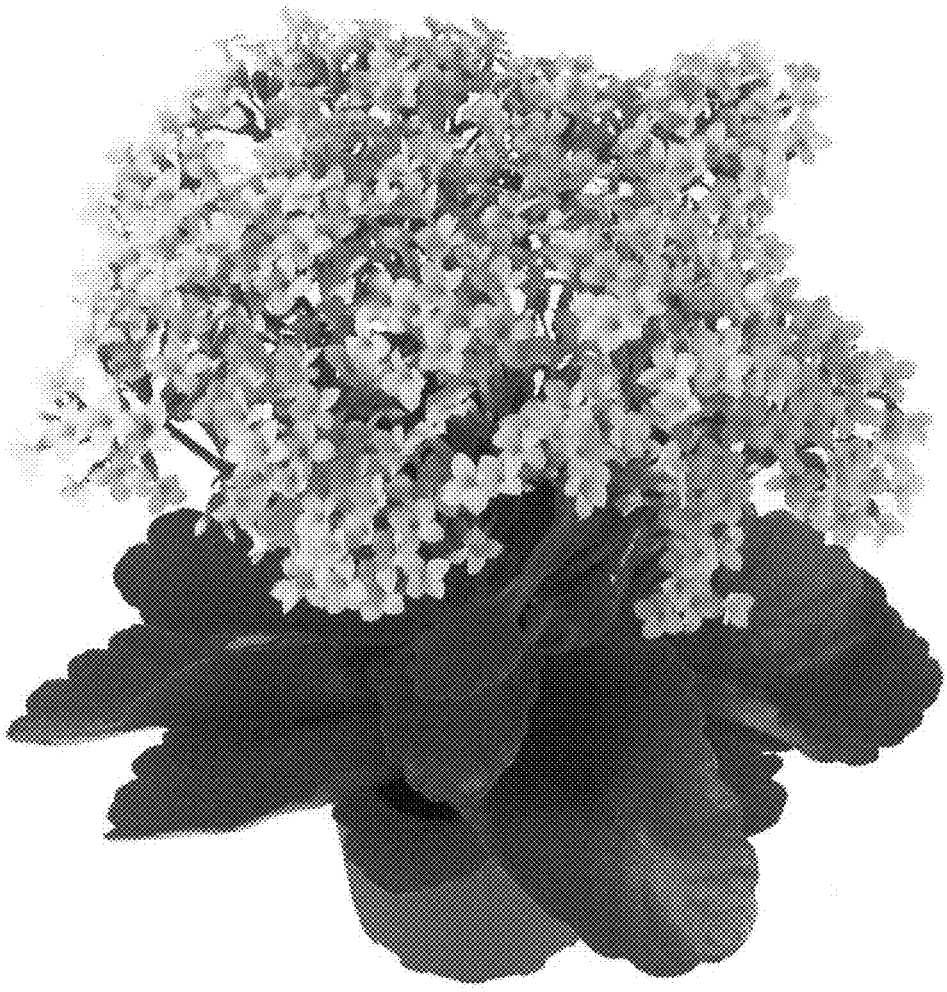

* * * * *